United States Patent [19]
Schmid

[11] Patent Number: 6,084,669
[45] Date of Patent: Jul. 4, 2000

[54] FLUORESCENT LIGHT MEASURING DEVICE AND AN APPARATUS WHEREIN SUCH A DEVICE IS USED

[75] Inventor: Karl Schmid, Pfäffikon, Switzerland

[73] Assignee: Roche Diagnostics Corporation, Indianapolis, Ind.

[21] Appl. No.: 09/303,376

[22] Filed: Apr. 30, 1999

[30] Foreign Application Priority Data

May 1, 1998 [EP] European Pat. Off. .............. 98810395

[51] Int. Cl.[7] ....................................................... C01J 3/42
[52] U.S. Cl. .............................. 356/319; 356/36; 356/445
[58] Field of Search ................................. 356/319, 36, 445

[56] References Cited

U.S. PATENT DOCUMENTS 5,096,807  3/1992  Leaback .

FOREIGN PATENT DOCUMENTS 0 608 932  8/1994  European Pat. Off. .
2 315 131  1/1998  United Kingdom .

*Primary Examiner*—Frank G. Font
*Assistant Examiner*—Reginald A. Ratliff
*Attorney, Agent, or Firm*—Gibbons, Del Deo, Dolan, Griffinger & Vecchione

[57] ABSTRACT

A device for simultaneously and/or group-wise random measuring fluorescent light emitted by sample-reagent mixtures contained in a plurality of reaction vessels.

In order to measure fluorescence light for each reaction vessel with high sensitivity and accuracy and at the lowest possible cost the device according to the invention has an array of photodiodes built on a chip. Each of the photodiodes of the array is configured to receive fluorescent light emitted by a sample-reagent mixture contained in one of said plurality of reaction vessels and to provide an output signal representative of the intensity of said fluorescent light. An integrated electronic circuit is connected to the said array of photodiodes for processing output signals provided by photodiodes of the array. The integrated electronic circuit is mounted on the chip on which the array of photodiodes is built.

The output of each of the photodiodes of the array of photodiodes is directly connected to a corresponding input of the integrated electronic circuit.

15 Claims, 8 Drawing Sheets

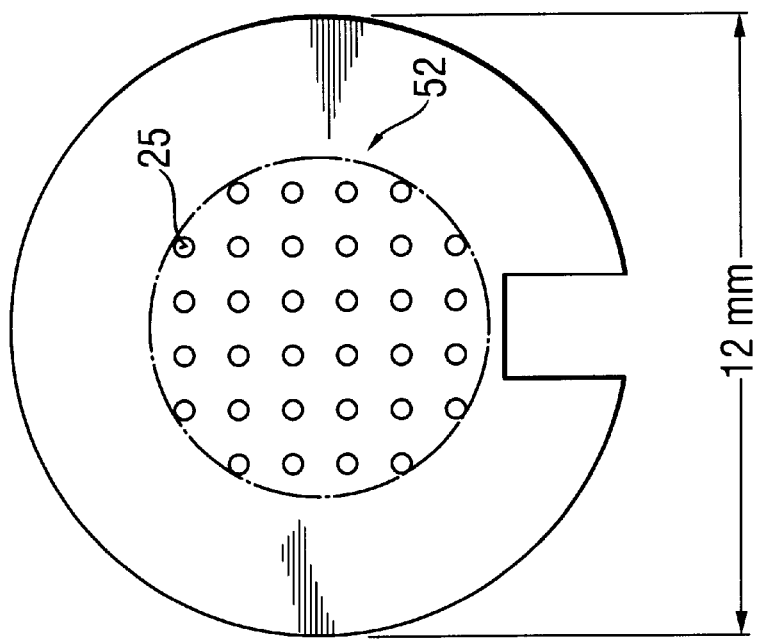
_Fig. 3_
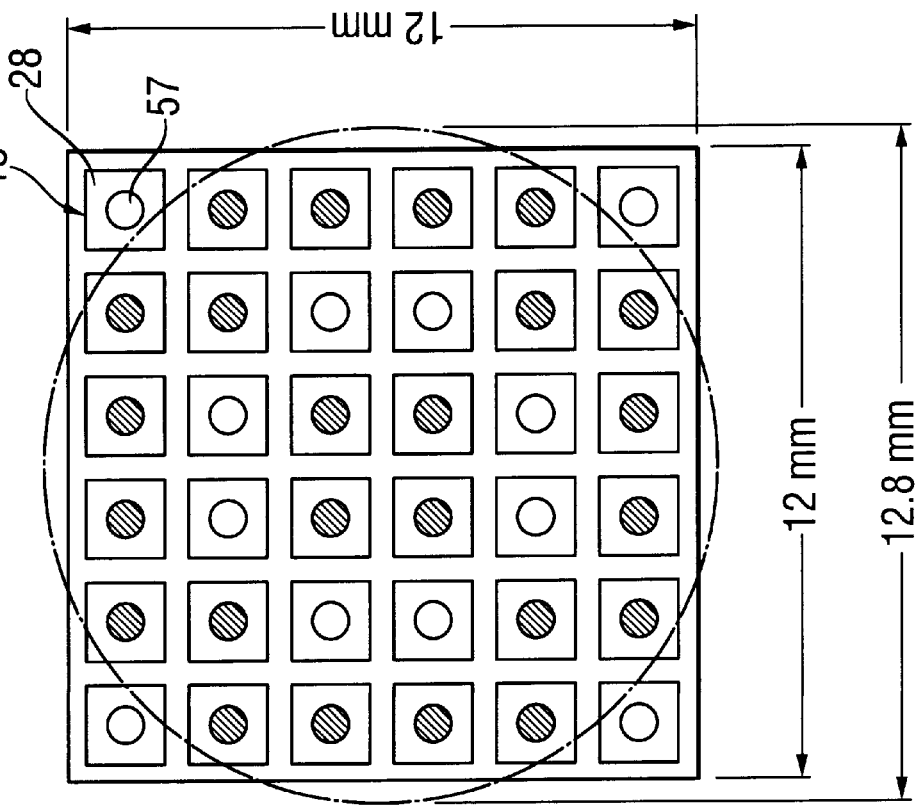
_Fig. 2_

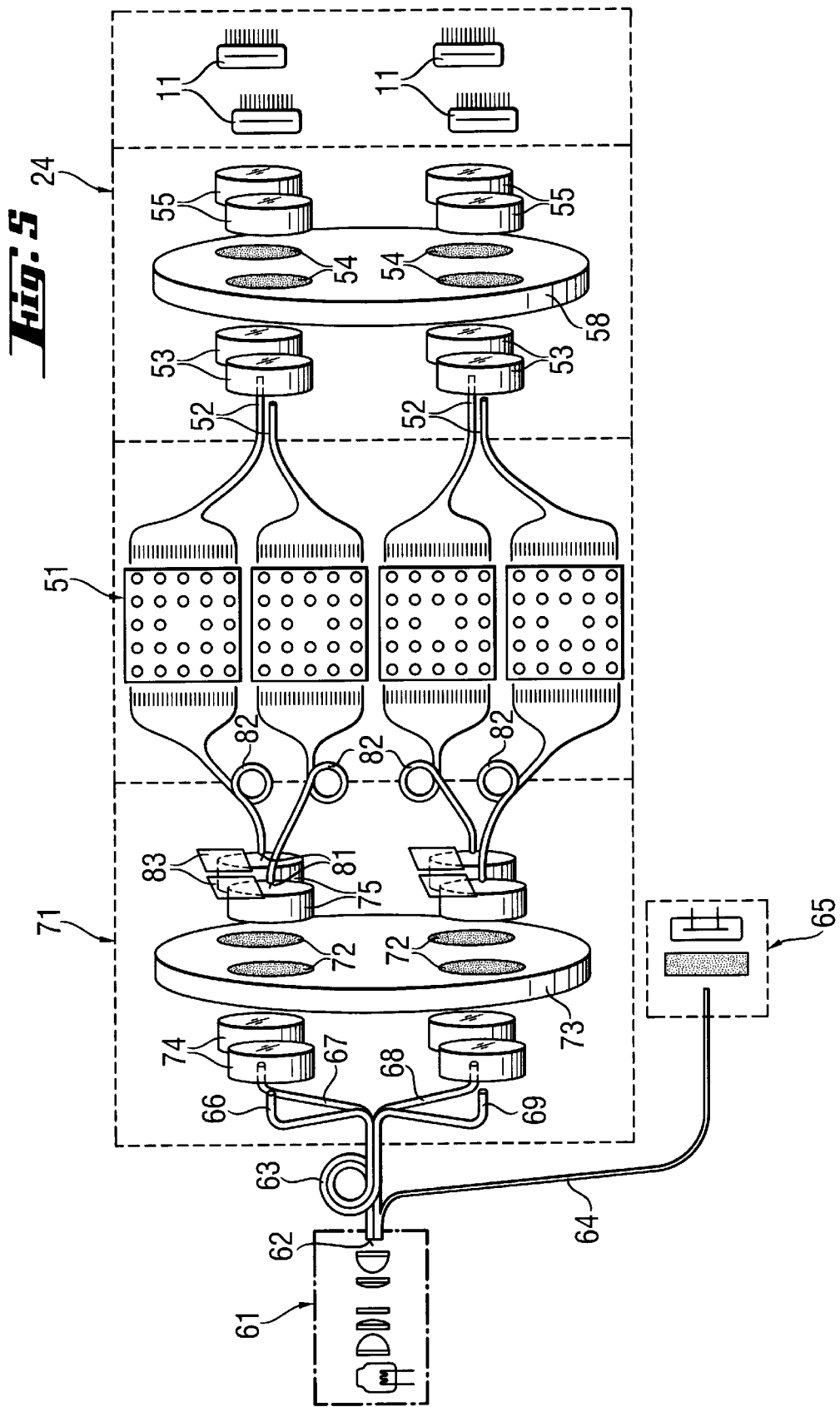

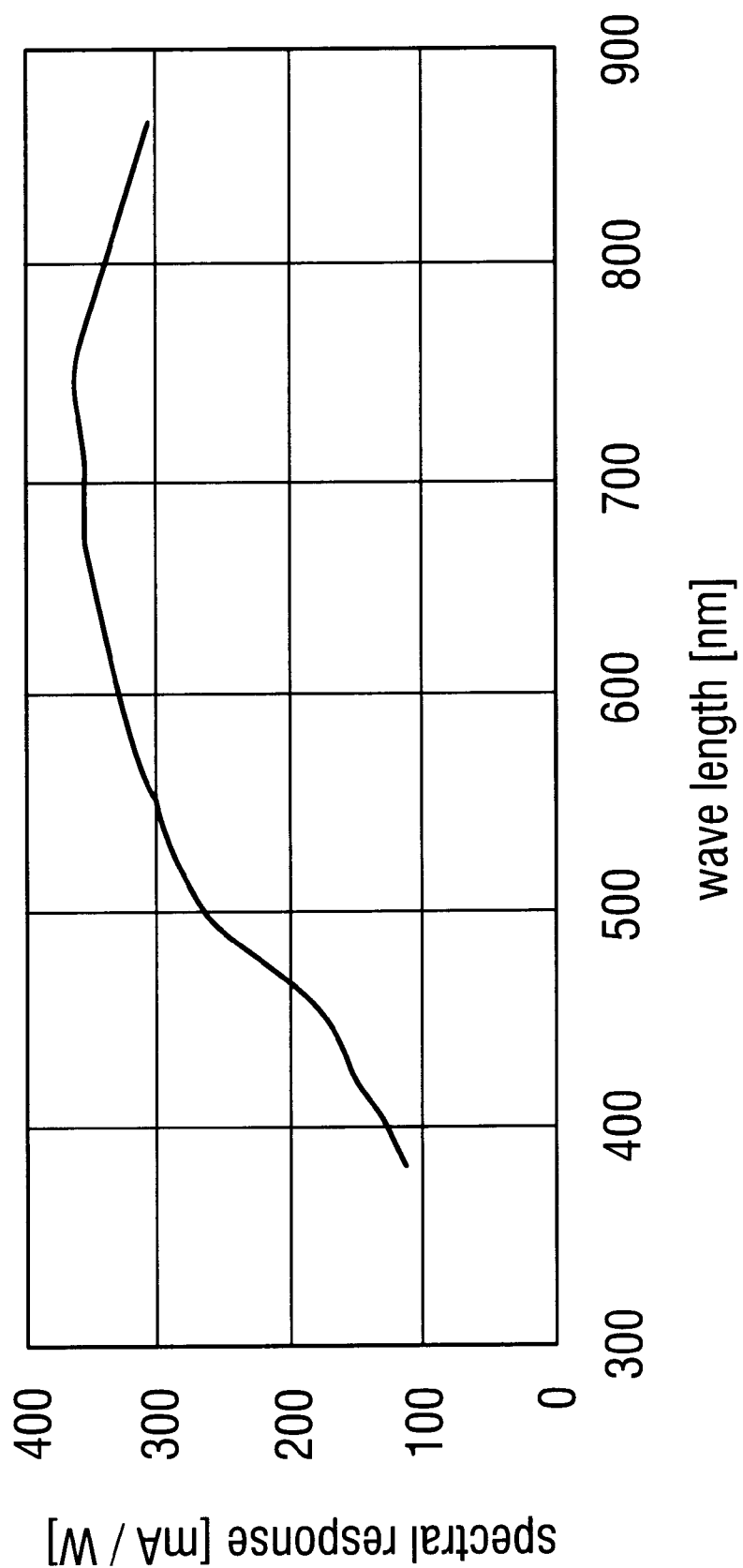

FLUORESCENT LIGHT MEASURING DEVICE AND AN APPARATUS WHEREIN SUCH A DEVICE IS USED

RELATED APPLICATIONS

This application is related to the European Patent Application No.98810395.8 filed on May 1, 1998.

BACKGROUND OF THE INVENTION

1. Field of the Invention

The present invention refers to a device for simultaneously measuring fluorescent light emitted by sample-reagent mixtures contained in a plurality of reaction vessels.

The invention further concerns an apparatus wherein such a device is used.

In order to measure fluorescent light emitted by sample-reagent mixtures contained in a plurality of reaction vessels simultaneously, it is necessary to convey fluorescent light beams emitted from all the reaction vessels in parallel to a corresponding plurality of light receivers, e.g. by means of a corresponding number of optic fibers. The output signals of the latter have to be processed by suitable electronic signal processing circuits in order to obtain the desired information from the fluorescent light detected with the light receivers.

Since intensity of fluorescent light to be measured is very low, it is mandatory that the detection system as a whole operates at a level of noise which is as low as possible.

An additional requirement is that the number of light receivers should be as small as possible in order to reduce the cost of the electronic and signal processing means and in order to increase read out speed.

A further requirement is that the price of the light receiver means is very low

2. Description of the Prior Art

Known prior art are unable to provide a solution which satisfies all of the above-mentioned requirements. Prior art use of charge coupled devices (CCDs) as light receivers makes it possible to operate at a relatively low level of noise, but CCDs are rather expensive if only a small number of pixels is required. Due to the high number of pixels of a CCD for fast read out, a CCD requires expensive electronic signal processing means. Use of a CCD becomes even more expensive if an integrated pixel binning function (reading of signals provided by a group of pixels) is used.

Another disadvantage of a CCD is that its quantum efficiency is low. This disadvantage can be diminished by use of a more expensive back-illuminated CCD or by adding an image intensifier in front of the CCD. This latter approach is not only very expensive, but in addition reduces the quantum efficiency.

Further disadvantages of a CCD are that, in general it has a poor dynamic range, and it only enables destructive reading of a pixel because the signal reading erases the signal being read (reset).

Another possible approach is the use of photomultiplier tube arrays (PMT-arrays) as light receiver means, but this type of arrays have a high level of cross-talk, are of relatively large size, and the additional external means necessary to reduce noise to an acceptable level are rather expensive.

Another possibility would be to use an array of discrete photodiodes as light receivers. This would be a cheap solution, but their high noise and/or high dark current makes such photodiodes wholly unsuitable for the measurement of fluorescent light within the context of the instant invention.

SUMMARY OF THE INVENTION

It is an object of the present invention to provide an apparatus and a method which makes it possible to overcome the above-mentioned disadvantages of conventional approaches for simultaneously and/or group-wise random measuring fluorescent light emitted by sample-reagent mixtures contained in a plurality of reaction vessels.

According to one embodiment, the present invention includes an array of photodiodes built on a chip. Each of the photodiodes of the array can receive fluorescent light emitted by a sample-reagent mixture contained in one of the plurality of reaction vessels and provides an output signal representative of the intensity of said fluorescent light.

An integrated electronic circuit connected to the array of photodiodes processes the output signals provided by photodiodes of the array.

An integrated electronic circuit is mounted on the chip on which the array of photodiodes is built.

The output of each of the photodiodes of the array of photodiodes is directly connected to a corresponding input of the integrated electronic circuit.

According to another embodiment of the present invention, the above-mentioned objective is attained with an apparatus for simultaneously and/or group-wise randomly measuring fluorescent light emitted by sample-reagent mixtures contained in a plurality of reaction vessels. This embodiment includes a plurality of optic fiber light guides each of which optically connects one of a plurality of reaction vessels with a photodiode of the array of photodiodes which is part of the apparatus.

This embodiment further includes means for optically connecting one end of each of the plurality of optic fiber light guides with a corresponding photodiode of the array of photodiodes. The optical connecting means is configured and dimensioned so that the fluorescence light emitted by a sample-reaction mixture contained in one of the reaction vessels and transmitted through one of the optic fiber light guides impinges on one of the photodiodes.

An advantage of the present invention is that a miniaturized structure of a device is obtained by combining in one chip a photodiode array and an application specific integrated electronic circuit (ASIC) for processing the output signals of the photodiodes of the array. The array of photodiodes are used as light receivers. This array is part of a device with an application specific integrated circuit (ASIC) which also includes an electronic circuit for processing and evaluating output signals of photodiodes.

Another advantage of the present inventions is that due to the integration of signal processing circuitry and a photodiode array in the same housing, a device according to the invention makes it possible to operate with a very low noise level, e.g., 0.5 fW/mm$^2$ light equivalent (with light of about 485 nm wavelength) with 2.5 seconds integration time without cooling.

A further advantage of the present invention is that compared with CCDs, PMT-Arrays and conventional photodiode arrays, a device according to the invention is substantially cheaper.

An additional advantage of the present invention is that the photodiodes, which are part of a device according to the invention, have a high quantum efficiency and a high linearity of operation.

Another advantage of the present invention is that with a device according to the invention a large dynamic range of measurement is obtained (e.g. about 400000 for one integrating period) by periodical sampling of those output signals before they reach their saturation level.

Additionally, since the number of pixels of the light receiver means used in a device according to the invention is relatively small, it is possible to electronically read and evaluate the output signals of those pixels with simple electronic means and at high speed, i.e. in a very short time.

Also, since each of the pixels of the photodiode array used in a device according to the invention is relatively of large size, it is possible to avoid the need for an optical adjustment of the specific illumination provided by fluorescent light generated in the corresponding reaction vessel.

A further advantage of the present invention is that the choice of a photodiode array as a basic component of a device according to the invention, provides a high quantum efficiency (e.g. a quantum efficiency larger than 50%), which helps to increase signal to shot noise ratio.

BRIEF DESCRIPTION OF THE DRAWINGS

FIG. 2 is a front view of the photodiode array.

FIG. 3 is a front view of a plurality of optic fiber light guides used for transmitting fluorescent light from a sample-reagent-mixture to a photodiode.

FIG. 5 is a schematic view of an apparatus according to the invention.

FIG. 9 is a diagram showing the spectral response of a photodiode.

DETAILED DESCRIPTION OF THE INVENTION

The present invention refers to a device for simultaneously measuring fluorescent light emitted by sample-reagent mixtures contained in a plurality of reaction vessels.

Figure 1:
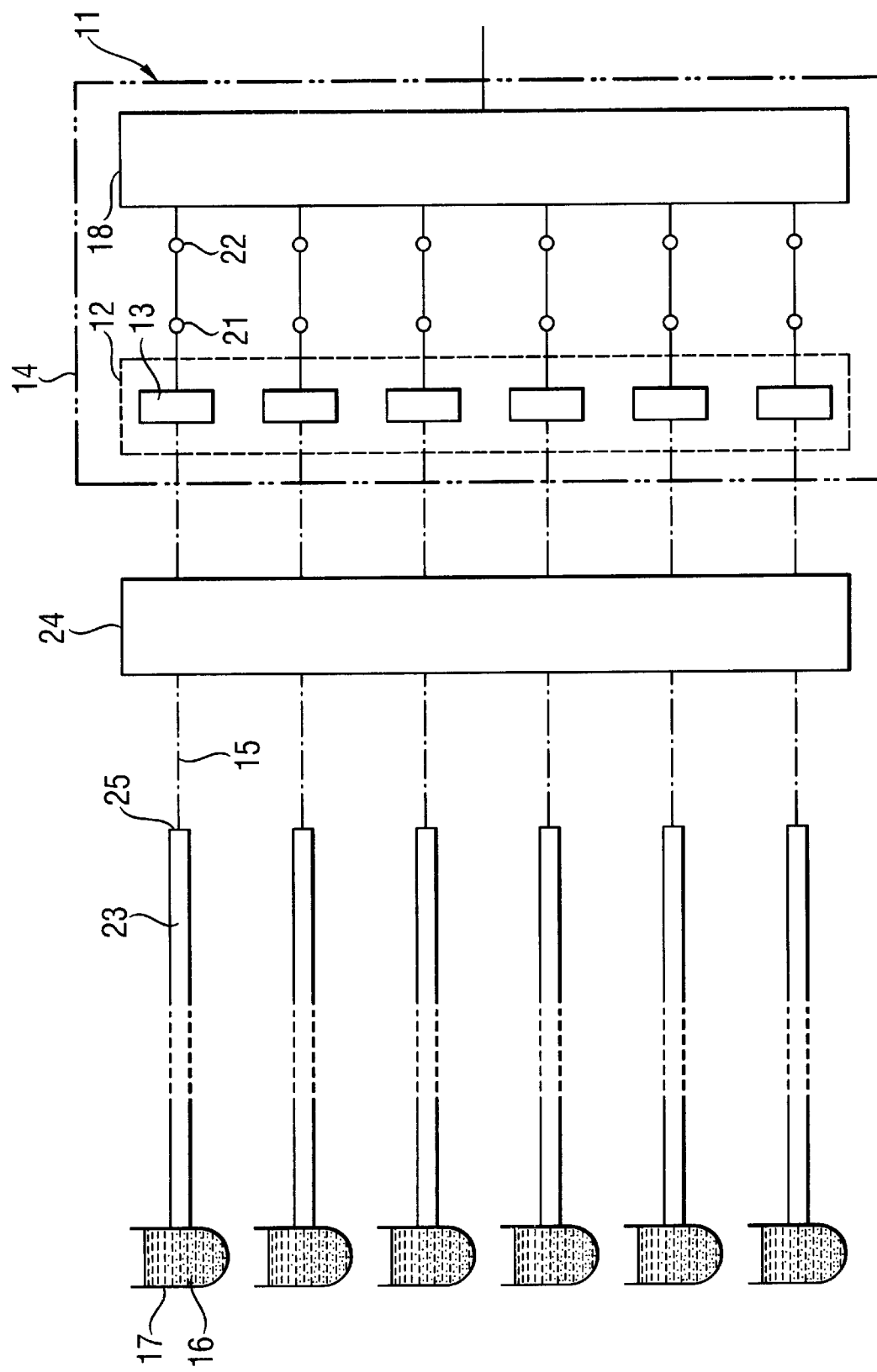
FIG. 1 is a schematic view of the invention and a partial view of an apparatus using the invention.

FIG. 1 illustrates a device 11 according to the present invention for simultaneously and/or group-wise random measuring fluorescent light emitted by sample-reagent mixtures 16 contained in a plurality of reaction vessels 17.

As shown in FIG. 1, the device 11 comprises an array 12 of photodiodes 13 built on a chip 14 and an integrated electronic circuit 18 connected to the array 12 of photodiodes 13 for processing output signals provided by the photodiodes 13. The outputs of the photodiode array are connected to inputs of the integrated electronic circuit 18 by means of very short connecting bond wires.

Figure 4:
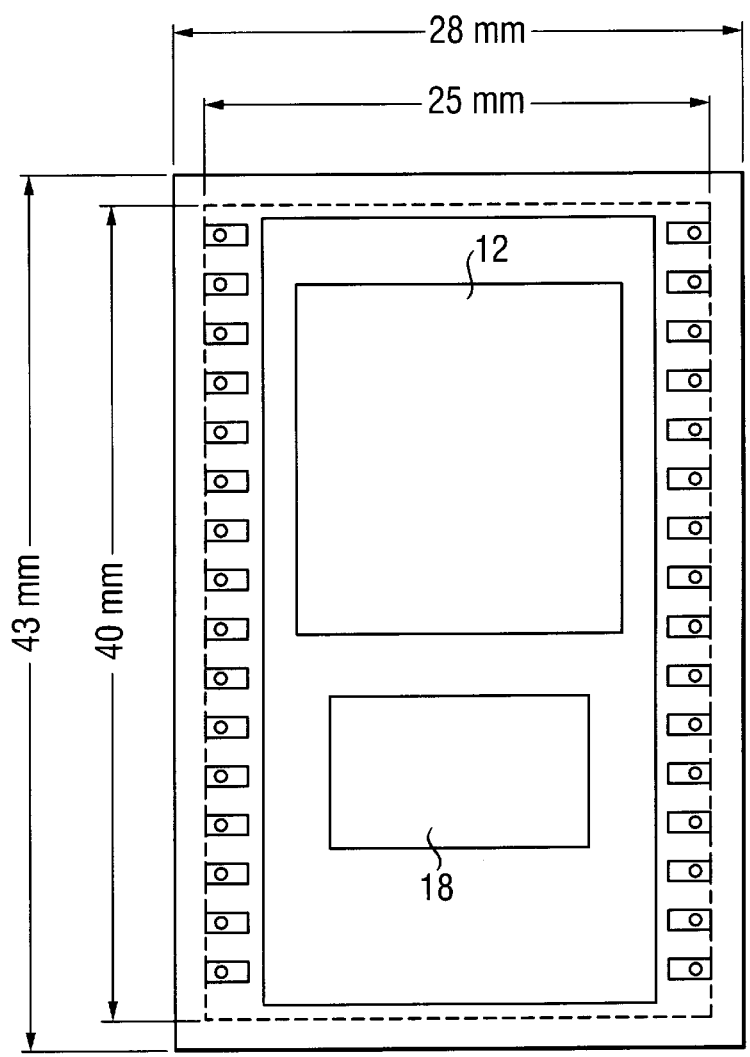
FIG. 4 is a top, side and front view of the external aspect of the invention.
Figure 4A:
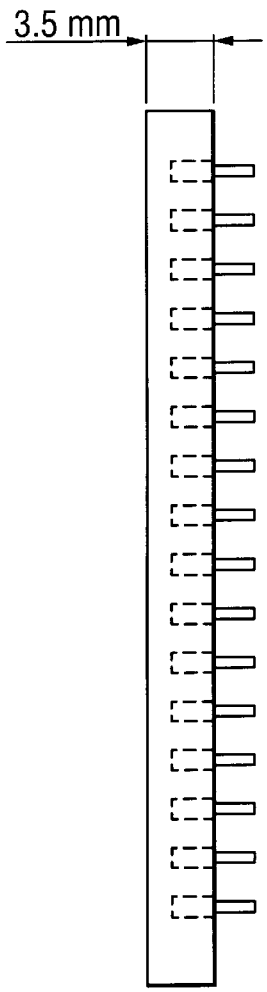
Figure 4B:
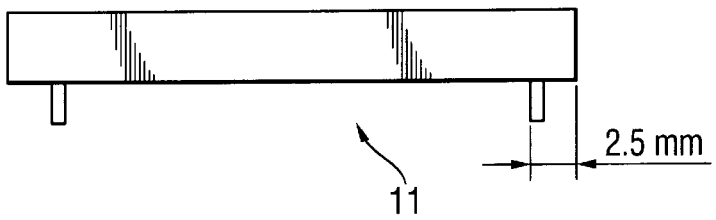

FIG. 4 shows the external dimensions of a preferred embodiment of the device 11 represented in FIG. 1.

Each of the photodiodes 13 of the array 12 can receive fluorescent light 15 emitted by a sample-reagent mixture 16 contained in one of a plurality of reaction vessels 17 and provide an output signal representative of the intensity of the fluorescent light 15. Some of the photodiodes of the array 12 are, however, not used for measuring fluorescent light by a sample-reagent mixture, but are used for different control purposes, e.g. to measure offset signal, the amount of stray light, scattered light, etc.

As shown in FIG. 2, which represents a front view of the photodiode array 12 represented in FIG. 1, in a preferred embodiment the photodiodes 13 of the array 12 are arranged in rows and columns in a matrix-like configuration.

The surface of each photodiode 13 of the array 12 shown in FIG. 2 is about 1.5×1.5 square mm and the separation between neighboring photodiodes 13 is about 0.5 mm.

In a preferred embodiment, the array 12 of photodiodes comprises a light absorbing mask 28 around each photodiode 13.

The light sensitive surface of the array 12 of the photodiodes is preferably not covered by a glass plate to avoid loss of light intensity which would otherwise be caused by such a glass plate.

The output 21 of each of the photodiodes 13 of the array 12 of the photodiodes is directly connected to a corresponding input 22 of the integrated electronic circuit 18.

The integrated electron ic circuit 18 is preferably mounted o n the same chip 14 on which the array 12 of the photodiodes 13 is built.

FIG. 5 shows a more complete representation of the apparatus shown in FIG. 1.

As can be seen from FIGS. 1 and 5, an apparatus according to the invention comprises a device 11 of the type described above, a plurality 52 of optic fiber light guides 23 each of which optically connects one of a plurality 51 of reaction vessels 17 with a corresponding photodiode 13 of array 12 of photodiodes 13 which is part of device 11, and optical means 24. Optical means 24 connect optically one end 25 of each of the plurality 52 of optic fiber light guides 23 with a corresponding photodiode 13 of the array 12 of photodiodes. Optical connecting means 24 are so con figured and dimensioned that every fluorescent light 15 beam emitted by a sample-reaction mixture 16 contained in one of the reaction vessels 17 and transmitted through one of the optic fiber light guides 23 impinges on one of the photodiodes 13.

In the apparatus represented in FIG. 5, a light beam provided by a light source 61, which includes a halogen lamp and suitable lenses for forming a light beam, is focused on the bundled end 62 of a bundle 63 of the optic fibers. A reference optic fiber 64 is separated from bundle 63 for light transmission to a light level and/or light level variation detector contained in a reference unit 65 for control purposes.

The remaining part of optic fiber bundle 63 splits into four optic fiber bundle branches 66 to 69. Light transmitted through each of these optic fiber bundle branches 66 to 69 is further transmitted by means of excitation filter module 71 which comprises a first set of movable filters 72 which are mounted on a filter wheel 73 and suitable optical lenses 74 and 75. Four light beams are transmitted through the excitation filter module 71. Each of these light beams is fed into the bundled end 81 of an optic fiber bundle 82. This fiber bundle divides into a plurality of optic fiber light guides each of which transmits excitation light to one of a plurality 51 of reaction vessels 17 positioned on a reaction vessel holder.

Each of the light channels transmitting light towards the reaction vessels is preferably closed by a shutter 83 in order to determine offset signal and dark current condition as well as for protecting the sample-reagent mixtures contained in the reaction vessels from unnecessary illumination.

In the example shown in FIG. 5, 24 separate fiber bundles lead fluorescent light emitted by sample-reagent mixtures contained in reaction vessels to optical means 24 which may be, for example, an emission filter module. Optical means 24 comprise a second set of movable filters 54 which are also mounted on a filter wheel 58 and suitable optical lenses 53 and 55.

Fluorescent light emitted by sample-reagent mixtures contained in each of the plurality 51 of reaction vessels positioned on a vessel holder is transmitted by optical means 24 to a corresponding photodiode 13 of the array 12 of photodiodes which is part of device 11 described above.

In a preferred embodiment of an apparatus according to the invention, the reaction vessels 17 contain a biological sample and at least one reagent in order to perform a diagnostic assay or analysis of that sample.

FIG. 3 shows a schematic representation of a front view of a plurality of ends 25 of the optic fiber light guides 23 represented in FIG. 1. Each is used for transmitting fluorescent light from a sample-reagent mixture 16 to a photodiode 13 of the array 12 of photodiodes.

As shown in FIG. 5, the optical connecting means 24 represented in FIG. 1 comprise an arrangement 53, 54 and 55 of optical lens means and optical filter means which are interposed between ends 25 of said plurality 52 of optical fiber light guides 23 and the corresponding photodiodes 13 of said photodiode array 12.

The optical connecting means 24 form an image of each of the plurality of ends 25 of the optic fiber light guides 23 represented in FIG. 3 on a corresponding photodiode 13 of the array 12 of photodiodes represented in FIG. 2.

In a preferred embodiment, the optical connecting means 24 are so configured and dimensioned that, as shown by FIG. 2, the spot 57 of each photodiode which is illuminated by the fluorescent light 15 is smaller than the active pixel size of the photodiode 13.

The integrated electronic circuit 18 represented in FIGS. 1 and 4 is so configured and dimensioned that it enables simultaneous and/or group-wise random measurement of fluorescence light emitted by sample-reagent mixtures 16 contained in a plurality of reaction vessels 17.

Figure 6:
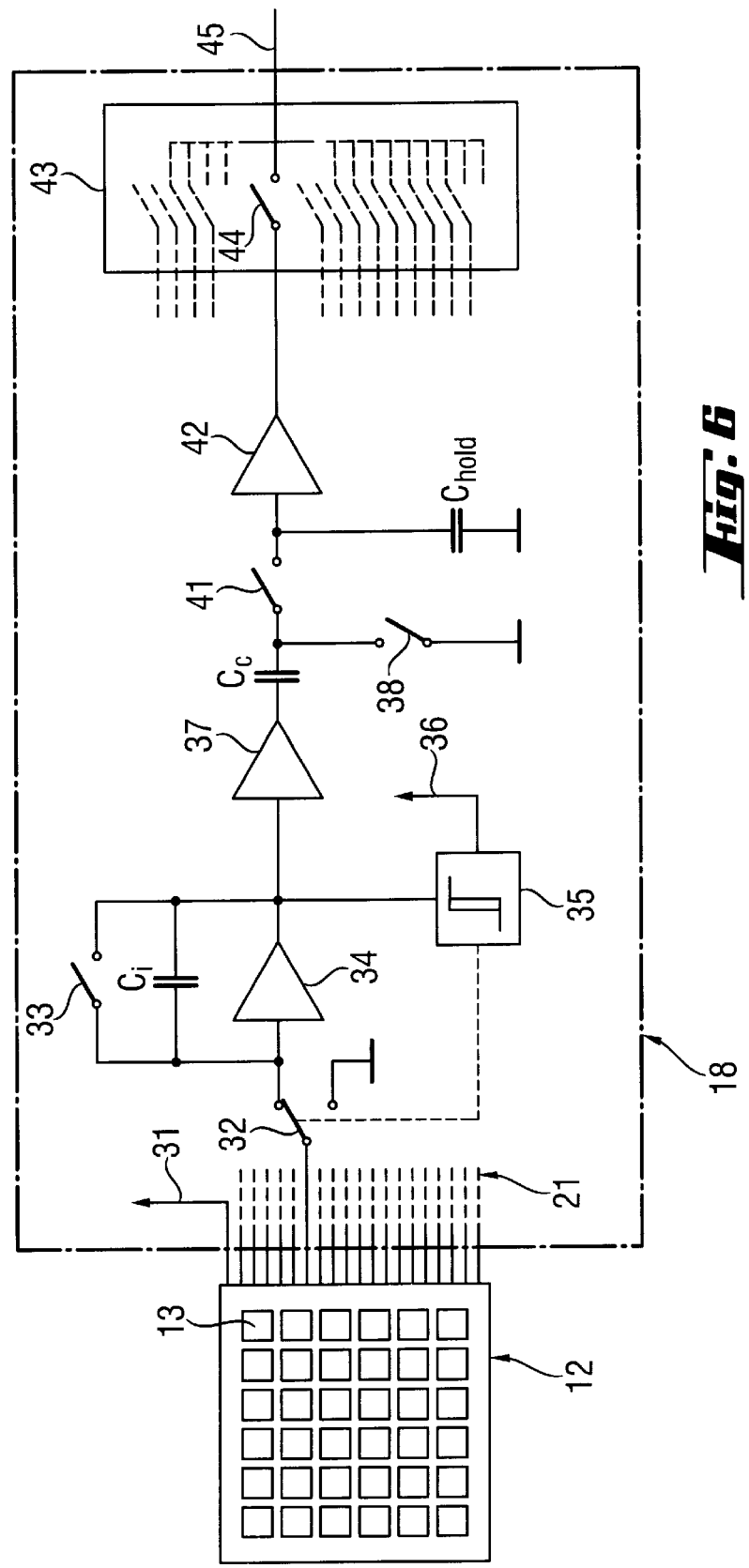
FIG. 6 is a schematic view of the photodiode array and a block diagram of the integrated electronic circuit.

FIG. 6 shows a schematic representation of the photodiode array 12 and a block diagram of the integrated electronic circuit 18 which are part of the device 11 represented in FIG. 1. Via a lead 31, the integrated electronic circuit 18 provides the necessary bias voltage for each of the photodiodes 13 of array 12. As shown in FIG. 6, a preferred embodiment of the integrated electronic circuit 18 comprises an integrating amplifier 34 including a reset switch 33 and an integrating capacitor $C_i$, an inverter 37, a clamp capacitor $C_c$, a clamp switch 38, a sample and hold circuit comprising a switch 41, a capacitor $C_{hold}$, and a high impedance amplifier 42. The integrated electronic circuit 18 amplifies and integrates the output signal of each of the photodiodes 13 of array 12 of photodiodes, and provides output signals obtained by sequential reading of the integrated output signals of the photodiodes. The integrated electronic circuit 18 is so configured and dimensioned that the sequential reading or the integrated output signals is a reading in a non-destructive mode. For this purpose, the output signal of the integrating amplifier is applied to the input of a sample and hold circuit without interfering with the integration process. This step can be repeated as many times as desired during the integration interval.

By means of the reset switch 33, the charge loaded on the capacitor $C_i$ used for the integrating process can be discharged to zero. This can be done for all photodiodes at a time.

Since the integrated electronic circuit 18 makes it possible to read the output signals of the photodiodes 13 of device 11 very fast and in an non-destructive mode, in a preferred embodiment the inverter 37, clamp capacitor $C_c$, clamp switch 38, a sample and hold circuit comprising a switch 41, capacitor $C_{hold}$, and high impedance amplifier 42 are used to carry out a sampling of the integrated signal during the integration process and to stabilize the end value of an output signal derived from the output of amplifier 42, e.g. by means of regression analysis and to compute the offset (start value).

In order to provide an output signal, e.g. a video signal, carrying the information obtained by sequential reading of the integrated output signals of the photodiodes, a preferred embodiment of integrated electronic circuit 18 further comprises electronic circuit means 43, e.g., a shift register, for multiplexing of the output signals of said first electronic circuit means. Electronic circuit means 43 comprise a plurality of switches 44.

A preferred embodiment of the integrated electronic circuit 18 further comprises an antiblooming circuit 35. This circuit prevents a charge overflow from one signal processing channel to other signal processing channels in the integrated circuit 18. This makes it possible to continue the integration of weak signals while ignoring strong intensities of other samples. To provide this effect, the antiblooming circuit 35 compares the level of the integrated signal with a selectable level received via a lead 36. When this level is reached, the antiblooming circuit 35 connects the output signal of the photodiode to the ground. By suitable selection of the selectable level, a very linear performance is obtained because not only the charge overflow of the circuit signal is prevented but also the saturation of the photodiode as well. Therefore, a very good linearity of the integrated signal can be obtained.

Figure 7:
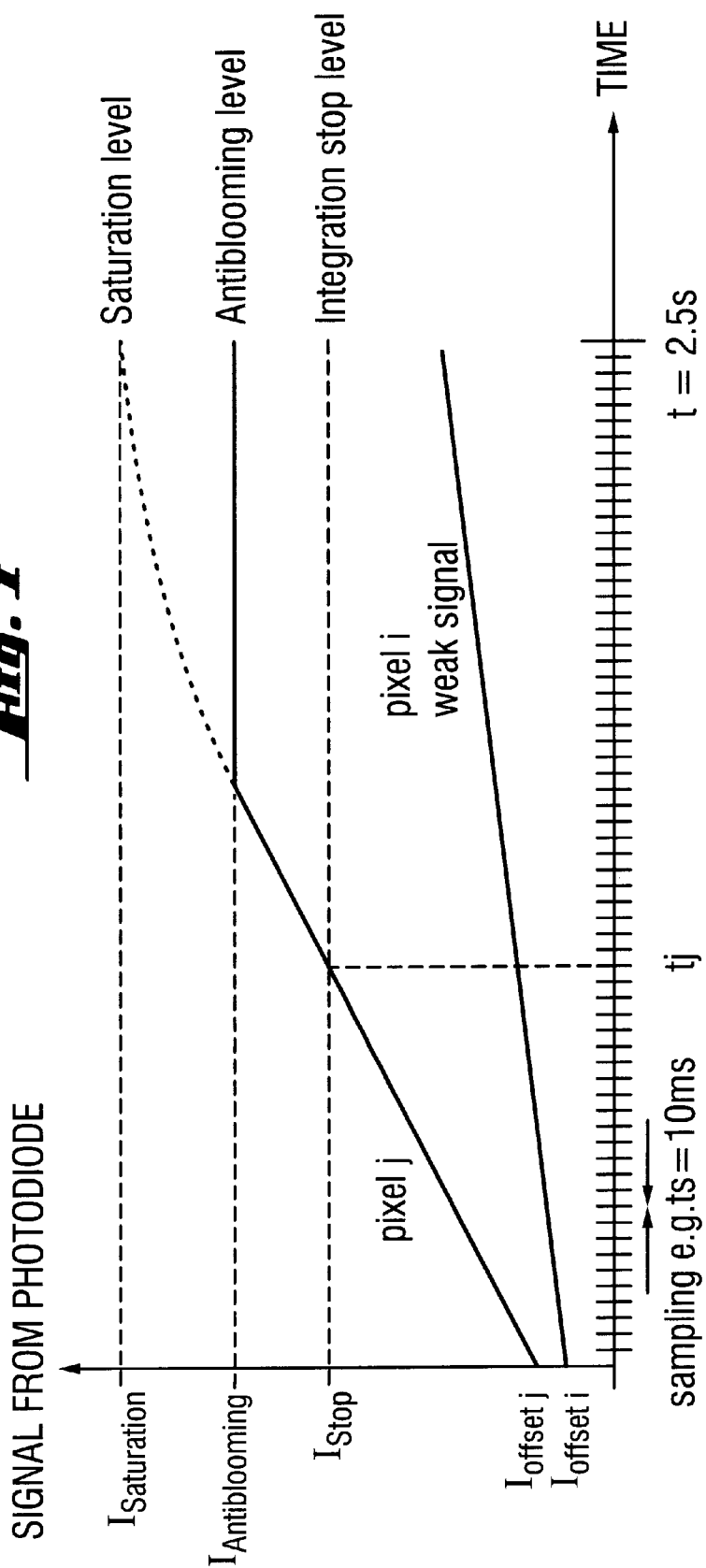
FIG. 7 is a signal diagram showing variation with time of output signals of a photodiode 13.

FIG. 7 is a signal diagram showing variation with time of the integrated output signals derived from the output signals of two different photodiodes of the array 12 represented in FIG. 1 which receive different intensities of fluorescent light. One of these signals is a weak signal which corresponds to a pixel i of a first photodiode. The other signal is a strong signal which corresponds to a pixel j of a second photodiode.

The strong integrated signal which corresponds to a pixel j would reach the saturation value before the end of an integration interval of 2.5 seconds. However, the above-described antiblooming circuit 35 ensures that this signal does not exceed a predetermined antiblooming level represented in FIG. 7. The measurement of the integrated signal which corresponds to a pixel j is terminated when a predetermined threshold value is reached.

Continuous reading of the signal which corresponds to a pixel j makes it possible to compute the offset and regression end value scaled with respect to the maximum value of the integration interval.

A weak integrated output signal like the one which corresponds to pixel i is integrated over the complete integration interval, because the antiblooming circuit does not interfere with the integration process of such a signal.

Figure 8:
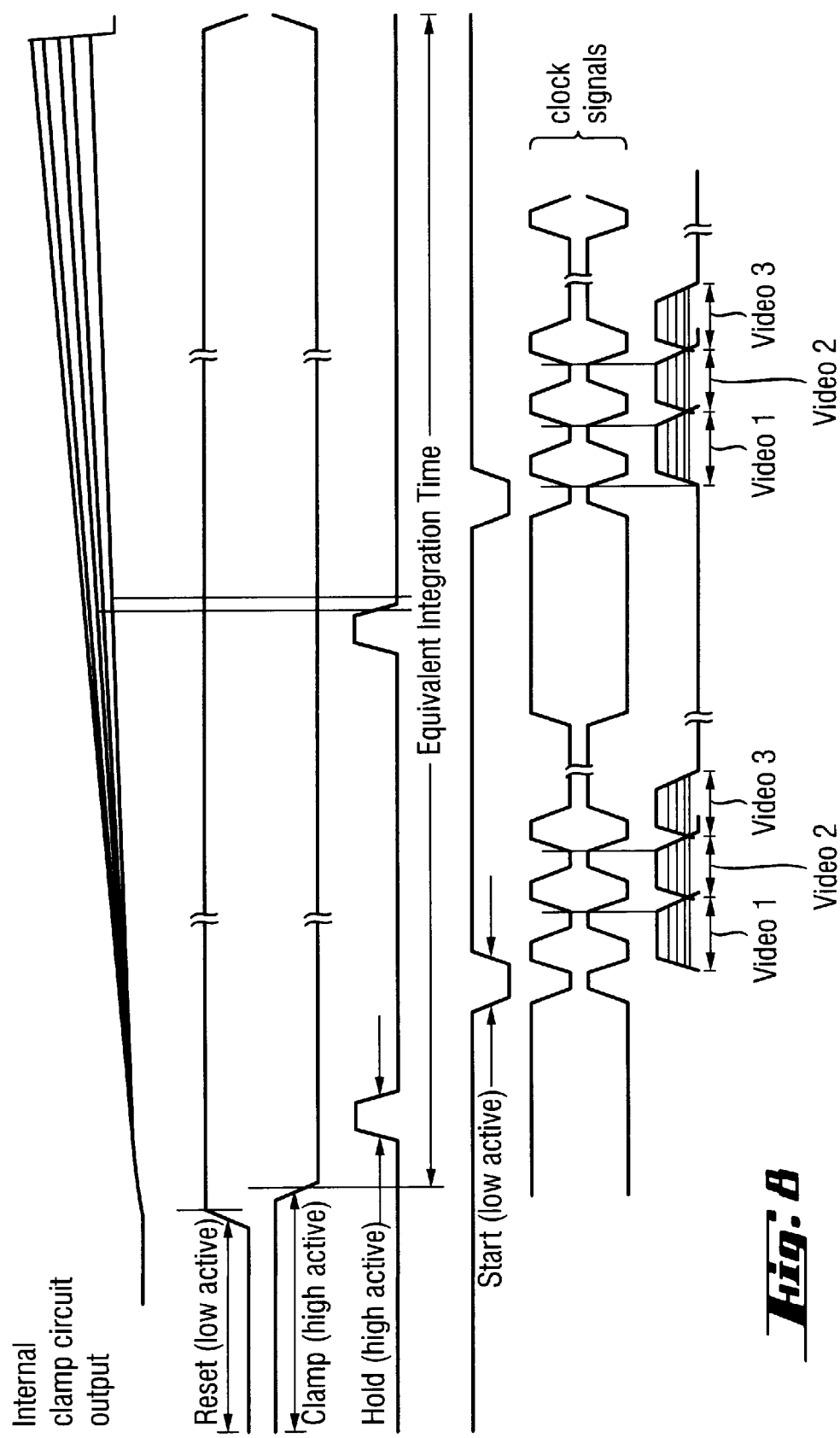
FIG. 8 is a signal diagram showing waveforms related to the operation of the integrated electronic circuit.

FIG. 8 is a signal diagram showing typical waveforms related to the operation of the integrated electronic circuit 18 represented in FIG. 1.

As shown in FIG. 8, at the beginning of the integration interval, the reset switch 33 and clamp switch 38 are set in their inactive position. During the integration interval, the output signal of the integrating amplifier 34 is sampled by briefly activating the hold switch 41 without interfering with the integration process of such a signal.

Eventually the sample values stored in a shift register 43 are read out by means of a start pulse and a clock signal and the signal generated in this way is a succession of pulses of a video signal.

Since the number of pixels to be read is relatively small, a low frequency clock pulse can be chosen. This makes it possible to read out the video signal with a relatively cheap analog/digital transducer and to obtain a high bit depth in spite thereof.

FIG. 9 represents a diagram showing the spectral response of a photodiode 13 represented in FIG. 1. This diagram shows that such a photodiode has a high quantum efficiency in the wavelength region, e.g. 500–750 nm, used in the above-described preferred embodiments.

It should be understood, however, that the present invention herein illustrated and described is intended to be representative only, as many changes may be made therein without departing with the clear teachings of the invention.

Accordingly, reference should be made to the following claims in determining the full scope of the invention, as it will be appreciated that the invention is susceptible to modification, variation and change without departing from the proper scope and fair meaning of the subjoined claims.

What is claimed is:

1. A device for measuring fluorescent light emitted by sample-reagent mixtures contained in a plurality of reaction vessels, said device comprising:

(a) an array of photodiodes built on a chip, wherein each of the photodiodes of the array is capable of receiving fluorescent light emitted by a sample-reagent mixture contained in one of said plurality of reaction vessels and providing an output signal representative of the intensity of said fluorescent light; and (b) an integrated electronic circuit connected to said array of photodiodes for processing output signals provided by said photodiodes of said array, said integrated electronic circuit being mounted on said chip on which said array of photodiodes is built and said integrated electronic circuit comprising first electronic circuit means for amplifying and integrating the output signals of said photodiodes and for providing output signals obtained by sequential reading of the integrated output signals, said sequential reading of the integrated output signals being a reading in non-destructive mode;

wherein output of each of said photodiodes of said array of photodiodes is directly connected to a corresponding input of said integrated electronic circuit.

2. A device according to claim 1, wherein the photodiodes of said array of photodiodes are arranged in rows and columns in a matrix-like configuration.

3. A device according to claim 1, wherein the surface of each photodiode of said array of photodiodes is about 1.5×1.5 square mm and the separation between neighboring photodiodes is about 0.5 mm.

4. A device according to claim 1, wherein said array of photodiodes further comprises a light absorbing mask around each photodiode.

5. A device according to claim 1, wherein said integrated electronic circuit is so configured and dimensioned that it enables simultaneous and/or group-wise random measurement of fluorescence light emitted by sample-reagent mixtures contained in a plurality of reaction vessels.

6. A device according to claim 1, wherein said integrated electronic circuit further comprises second electronic circuit means for multiplexing of the output signals of said first electronic circuit means.

7. A device according to claim 1, wherein said first electronic circuit means further comprises means to sample the integrated signal during the integration process and to compute the value of an end signal by regression analysis of the sampled values.

8. A device according to claim 1, wherein said first electronic circuit means further comprise means for preventing blooming.

9. An apparatus for simultaneously and/or group-wise random measuring fluorescent light emitted by sample-reagent mixtures contained in a plurality of reaction vessels, said apparatus comprising:

(a) an array of photodiodes built on a chip, each of the photodiodes of the array can receive fluorescent light emitted by a sample-reagent mixture contained in one of said plurality of reaction vessels and to provide an output signal representative of the intensity of said fluorescent light;

(b) an integrated electronic circuit connected to said array of photodiodes for processing output signals provided by photodiodes of said array, said integrated electronic circuit being mounted on said chip on which said array of photodiodes is built; the output of each of the photodiodes of said array of photodiodes being directly connected to a corresponding input of said integrated electronic circuit;

(c) a plurality of optic fiber light guides each of which optically connects one of a plurality of said reaction vessels with said photodiode; and (d) means for optical connecting one end of each of said plurality of optic fiber light guides with a corresponding photodiode of said array of photodiodes, said optical connecting means being so configured and dimensioned that fluorescent light emitted by a sample-reaction mixture contained in one of said reaction vessels and transmitted through one of said optic fiber light guides impinges on one of said photodiodes.

10. An apparatus according to claim 9, wherein said reaction vessels contain a biological sample and at least one reagent in order to perform a diagnostic assay or analysis of that sample.

11. An apparatus according to claim 9, wherein said optical connecting means comprise an arrangement of optical lens means and optical filter means which are interposed between said ends of said plurality of optical fiber light guides and the corresponding photodiodes of said photodiode array.

12. An apparatus according to claim 9, wherein said optical connecting means are so configured and dimensioned that the spot of each photodiode which is illuminated by the fluorescence light is smaller than the active pixel size of the photodiode.

13. A device according to claim 2, wherein the surface of each photodiode of said array of photodiodes is about 1.5×1.5 square mm and the separation between neighboring photodiodes is about 0.5 mm.

14. A device according to claim 2, wherein said array of photodiodes further comprises a light absorbing mask around each photodiode.

15. A device according to claim 3, wherein said array of photodiodes further comprises a light absorbing mask around each photodiode.

* * * * *